United States Patent [19]

Blattner et al.

[11] 4,171,366
[45] Oct. 16, 1979

[54] 1-NAPHTHOTHIENYLALKYL-1H-IMIDAZOLES

[75] Inventors: Hans Blattner, Riehen; Angelo Storni, Rheinfelden, both of Switzerland

[73] Assignee: Ciba-Geigy Corporation, Ardsley, N.Y.

[21] Appl. No.: 854,935

[22] Filed: Nov. 25, 1977

[30] Foreign Application Priority Data

Dec. 1, 1976 [LU] Luxembourg .......................... 76303

[51] Int. Cl.² ................. A61K 31/415; C07D 409/10; C07D 409/06
[52] U.S. Cl. ............................ 424/273 R; 548/335; 548/336
[58] Field of Search ..................... 548/336; 424/273 R

[56] References Cited

U.S. PATENT DOCUMENTS 3,903,092  9/1975  Chapman et al. ..................... 548/336

OTHER PUBLICATIONS

Draber et al., Chem. Abst. 1972, vol. 76, No. 59632e.
Clarke et al., J. Chem. Soc. 1973, Perkin Transactions I, pp. 2956–2960.
Draber et al., Chem. Abst. 1970, vol. 73, No. 45510q.
Timmler et al., Chem. Abst. 1972, vol. 76, No. 3862w.
Buechel et al., Chem. Abst. 1972, vol. 76, No. 72516q.
Van der Stelt, Chem. Abst. 1972, vol. 76, No. 99671y.
Chem. Abst. 1972, vol. 77, No. 34523c & 48464w.
Draber et al., Chem. Abst. 1976, vol. 84, No. 150629k.
Timmler et al., Chem. Abst. 1976, vol. 85, No. 58083a & 58084b.

*Primary Examiner*—John M. Ford
*Assistant Examiner*—Natalia Harkaway
*Attorney, Agent, or Firm*—John J. Maitner

[57] ABSTRACT

The present invention provides imidazole derivatives of the formula I

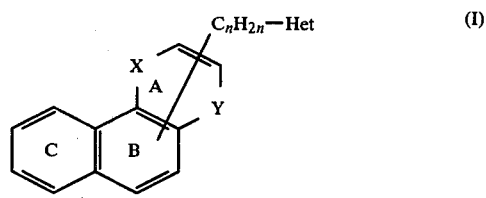

wherein
  Het represents 1H-imidazol-1-yl which is unsubstituted or is substituted by lower alkyl,
  one of the symbols X and Y represents the epithio radical -S- or the ethenylene group —CH=CH—, and the other represents the direct bond, and
  n represents 1 to 4, and the rings A and B, besides being substituted by the radical -$C_nH_{2n}$-Het, are not substituted or are further substituted, and the ring C is unsubstituted or substituted, and the monoacid acid addition salts, in particular the pharmaceutically acceptable monoacid acid addition salts thereof.

These new substances possess valuable pharmacological properties, in particular antidepressant activity, and can be used for the treatment of mental depressions. Specific embodiments are 1-[(naphtho[1,2-b]thien-4-yl)-methyl]-1H-imidazole and its pharmaceutically acceptable monoacid acid addition salts, and pharmaceutical compositions containing them.

16 Claims, No Drawings

1-NAPHTHOTHIENYLALKYL-1H-IMIDAZOLES

The present invention relates to new imidazole derivatives having valuable pharmacological properties, to processes for producing these new compounds, and to pharmaceutical compositions containing them.

The new imidazole derivatives according to the invention correspond to the general formula I

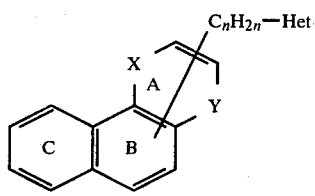

wherein
Het represents 1H-imidazol-1-yl which is unsubstituted or is substituted by lower alkyl,
one of the symbols X and Y represents the epithio radical —S— or the ethenylene group —CH=CH—, and the other represents the direct bond, and
n represents 1 to 4,
the rings A and B, besides being substituted by the radical —$C_nH_{2n}$—Het, are not substituted or are further substituted, and the ring C is unsubstituted or substituted. The invention relates also to the monoacid acid addition salts of the compounds of the general formula I, particularly to the pharmaceutically acceptable acid addition salts. By lower radicals are meant, in the foregoing and in the following, radicals having at most 7, preferably at most 4, carbon atoms.

Depending on the meaning of X and Y, the tricyclic ring system in the compounds of the general formula I is phenanthrene, naphtho[2,1-b]thiophene and, in particular, naphtho[1,2-b] thiophene. The radical Het is 1H-imidazol-1-yl, which can be mono- to trisubstituted by lower alkyl, such as by ethyl, propyl, isopropyl, butyl, isobutyl, sec.-butyl, tert.-butyl, pentyl, iospentyl, hexyl, isohexyl or heptyl, especially ethyl and above all methyl, and in the case of polysubstitution preferably at least one substituent is methyl. Suitable substituents of the ring C are, e.g., halogen such as fluorine, bromine and especially chlorine; lower alkyl such as ethyl, propyl, isopropyl, butyl, isobutyl, tert.-butyl, pentyl, neopentyl, tert.-pentyl, hexyl, heptyl and in particular methyl; lower alkoxy such as ethoxy, propoxy, isopropoxy, butoxy, isobutoxy and especially methoxy; and lower alkylthio such as ethylthio, propylthio, isopropylthio, butylthio, isobutylthio and in particular methylthio.

Suitable substituents or further substituents of the rings A and B are, for example, likewise the radicals mentioned as substituents of the ring C, with substituents of the ring A being in particular chlorine and methyl, and an additional substituent of the ring B being especially chlorine, methyl or methoxy. According to the meaning of n, the radical —$C_nH_{2n}$— is for example ethylene, trimethylene, propylene, tetramethylene or 2-methyltrimethylene, preferably ethylidene and above all methylene.

Suitable monoacid acid addition salts of the compounds of the general formula I are, for example, those with hydrochloric acid, hydrobromic acid, sulphuric acid, phosphoric acid, perchloric acid, methanesulphonic acid, ethanesulphonic acid, acetic acid, lactic acid, succinic acid, fumaric acid, maleic acid, malic acid, tartaric acid, citric acid, benzoic acid, salicyclic acid, phenylacetic acid, mandelic acid and embonic acid.

The compounds of the general formula I and their monoacid acid addition salts possess valuable pharmacological properties. As is seen from the results of the isotopic determination of the enzyme activity, they inhibit mono-amine oxidase in rats, in particular selectively and, without accumulation, reversibly the A-form thereof, after oral administration of doses down to 1 mg/kg. At the same time, the compounds of the general formula I, such as 1-[(naphtho[1,2-b]thien-4-yl)-methyl]-1H-imidazole, and the pharmaceutically acceptable monoacid acid addition salts thereof antagonise when administered to the rat orally in doses down to 3 mg/kg hypothermia produced by reserpine; and antagonise when administered orally in each case in doses down to about 10 mg/kg ptosis produced by reserpine, and, especially after pretreatment intervals of 18 or 24 hours, catalepsy produced by tetrabenazine. Together with a favourable therapeutic index, the pharmacological properties which are mentioned above characterise the compounds of the general formula I and their pharmaceutically acceptable monoacid acid addition salts as antidepressants which can be administered, e.g. orally or parenterally, for the treatment of mental depression.

The invention relates in particular to compounds of the general formula I wherein Het, X, Y and n have the meanings given under this formula, and in addition to the substitution of ring A or especially ring B by the radical $C_nH_{2n}$—Het, ring A is substituted by chlorine or methyl, is preferably however unsubstituted, ring B is substituted by chlorine, methyl or methoxy, is preferably however not further substituted, and ring C is unsubstituted or is monosubstituted by halogen up to atomic number 35, trifluoromethyl, lower alkyl, lower alkoxy or lower alkylthio, and to the monoacid acid addition salts of these compounds. The invention relates especially to compounds of the general formula I wherein Het is methylsubstituted 1H-imidazol-1-yl or preferably unsubstituted 1H-imidazol-1-yl, and n is 2 or preferably 1, X and Y have the meanings given under the formula I, and the rings A and B, in addition to substitution, preferably of the ring B, by the radical —$C_nH_{2n}$—Het, are not substituted or not further substituted, and ring C is unsubstituted or is monosubstituted in the aforementioned manner, particularly by chlorine, and to the monoacid acid addition salts thereof, especially to the pharmaceutically acceptable monoacid acid additions salts thereof. The present invention relates above all to compounds of the general formula I wherein Het is unsubstituted 1H-imidazol-1-yl and n is 1, and the [(1H-imidazol-1-yl)-methyl] radical corresponding to these meanings is preferably bound to ring B, one of the symbols X and Y, preferably X, represents epithio and the other symbol, preferably Y, represents the direct bond, and the rings A, B and C are not substituted or not further substituted, and to the monoacid acid addition salts thereof, particularly to the pharmaceutically acceptable monoacid acid addition salts thereof, such as the hydrochlorides and the methanesulphonates. In the compounds of the last-mentioned type, the [(1H-imidazol-1-yl)-methyl] radical is preferably bound to the 4-position of the tricycle, as is the case with the 1-[(naphtho[1,2-b]thien-4-yl)-methyl]-1H-imidazole to be particularly emphasised.

The new imidazole derivatives of the general formula I and their monoacid acid addition salts are produced according to the invention by
(a) reacting a reactive ester of a hydroxyl compound of the general formula II

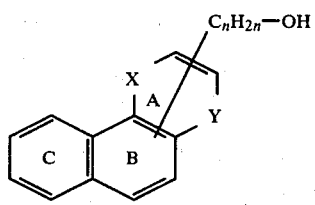

wherein X, Y and n have the meanings given under the formula I and the rings A, B and C are optionally substituted or further substituted, with a compound of the general formula III H—Het     (III)

in which Het has the meaning given under the formula I, or with an N-metal compound thereof; or
(b) treating a compound of the general formula IV

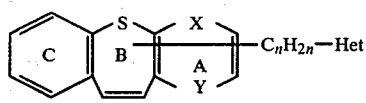

in which Het, X, Y and n have the meanings given under the formula I and the rings A, B and C are optionally substituted or further substituted, with an agent splitting off sulphur; and optionally converting a compound of the general formula I, obtained according to (a) or (b), into a monoacid acid addition salt, or liberating from an acid addition salt obtained the compound of the general formula I.

Suitable reactive esters of hydroxyl compounds of the general formula II are, for example, hydrohalic acid esters, such as corresponding bromides, iodides and chlorides, and also esters with other strong acids, particularly esters with organic sulphonic acids, e.g. lower alkanesulphonic acid esters such as methanesulphonic acid esters, and arenesulphonic acid esters such as benzene sulphonic acid esters and p-toluenesulphonic acid esters. The reactions with compounds of the general formula III, i.e., with 1H-imidazole and with its derivatives that are mono- to tri-lower-alkylated on ring carbon atoms, are performed preferably with use of an excess of these compounds, or in the presence of another acid-binding agent, in an organic solvent or solvent mixture inert under the reaction conditions. Reactions in particular with chlorides are if necessary accelerated by the addition of an alkali metal iodide, such as potassium iodide. Solvents which can be used are, for example, aromatic hydrocarbons such as benzene or toluene, lower alkanols such as methanol, ethanol, isopropanol or butanol, ethereal solvents such as dioxane, tetrahydrofuran or 2-methoxyethanol, lower aliphatic ketones such as ethyl methyl ketone, and N-substituted acid amides such as N,N-dimethylformamide or N,N,N',N',N",N"-hexamethylphosphoric acid triamide, and solvent mixtures which can be used are, e.g., those of aromatic hydrocarbons with lower alkanols, such as benzene together with a small amount of methanol. Suitable acid-binding agents are tertiary organic bases, such as triethylamine, pyridine, sym. collidine and in particular ethyldiisopropylamine; also alkali metal lower alkoxides such as sodium methoxide or sodium ethoxide, preferably in the corresponding lower alkanol as the sole or additional solvent; or inorganic basic substances, such as sodium hydroxide or potassium hydroxide or sodium carbonate or potassium carbonate. The reaction temperature is between about 0° and 200° C., preferably between room temperature and about 120° C.

Reactions of N-metal compounds of compounds of the general formula III, e.g. N-alkali metal compounds such as N-sodium or N-lithium compounds, or N-magnesium-bromide compounds, also for example N-silver compounds, with reactive esters of compounds of the general formula II are performed for example in an aromatic hydrocarbon such as benzene, or in an ethereal solvent such as diethyl ether, dioxane and particularly tetrahydrofuran, at temperatures between about 0° C. and 100° C. and if necessary in a closed vessel, preferably at slightly elevated temperatures of about 35° C. to 60° C. The N-metal compounds required are produced from the compounds of the general formula III preferably directly before their further reaction in the solvent provided for these, i.e., in situ, with the use of alkali metals or of amides or hydrides thereof, such as sodium, sodium amide, sodium hydride or lithium amide, or of lower alkyl-magnesium-bromide.

For the splitting-off of sulphur (sulphur extrusion) and for ring narrowing according to process (b), it is possible to apply the customary agents splitting off sulphur and the appertaining reaction conditions, e.g. tri-lower-alkylphosphites, especially triethylphosphite, in considerable excess as sole reaction medium, or in an inert organic solvent, e.g. in an aromatic hydrocarbon such as benzene, toluene, xylene or 1,2,3,4-tetrahydronaphthalene, at room temperature, or if necessary in a closed vessel at elevated temperatures up to about 200° C., preferably at about 60° C.; also, e.g., phosphorus oxychloride on its own or in, e.g., the aforementioned solvents, or in hydrocarbon halides, such as chloroform, trichloroethylene or chlorobenzene, and in the aforementioned temperature range. Further suitable agents splitting off sulphur are phosphines, such as triphenylphosphine and tri-lower-alkylphosphines, which are used together with bases. Triphenylphosphine is applied, e.g., together with a tertiary organic base, such as triethylamine, and if necessary with a catalyst, such as lithium perchlorate, likewise in the aforementioned solvents and in the aforesaid temperature range; and instead of the mixture of triphenylphosphine and organic base, it is also possible to use a basic phosphine, such as bis-[3-(dimethylamino)-propyl]-phenylphosphine. A further suitable solvent is for example acetonitrile, and a further suitable catalyst is for example lithium bromide, e.g. together with a basic phosphine, such as with the aforementioned basic phospine. Together with triphenylphosphine or with tri-lower-alkylphosphines, such as tributylphosphine, it is possible to use as bases also lower alkoxides of alkali metals, such as sodium tert.butoxide or, in particular, potassium tert.pentoxide, in an inert organic solvent, especially in an aromatic hydrocarbon such as benzene, likewise at room temperature or at moderately elevated temperature, preferably at about 60° C.

Furthermore, the splitting-off of sulphur can be effected by heating with copper powder, e.g. at a temperature of between 200° and 300° C., preferably at about 240° to 270° C., or with Raney nickel having a low hydrogen content.

Sulphur is split off however in a particularly advantageous manner above all in compounds of the general formula III wherein X represents epithio by heating with an alkali metal hydroxide, preferably at temperature between 160° and 220° C., in a protonic organic solvent, such as ethylene glycol, 2-methoxyethanol, 2-ethoxyethanol or diethylene glycol monomethyl ether, or alternatively in a closed vessel in a lower alkanol, such as ethanol, isopropanol or butanol.

A number of starting materials for the process (a), reactive esters of compounds of the general formula II in which X or Y represents the ethenylene group, are known, such as 9-(chloromethyl)- and 9-(bromomethyl)-phenanthrene, also mono-, di- and trimethoxy derivatives thereof, in connection with the synthesis of cryptopleurine and analogs, also 9-(bromomethyl)-6-chlorophenanthrene (see Tetrahedron, 27, 3465–3476), 2,6-bis-(trifluoromethyl)-9-(bromomethyl)-phenanthrene (see Chem. Abstr. 81, 169678 k), 9-(2-chloroethyl)-phenanthrene (see J. Amer. Chem. Soc. 58, 1678–1681) and p-toluenesulphonic acid-[2-(9-phenanthryl)-ethyl] ester [J. Amer. Soc. 92, 3996–4002 (1970)]. Further such starting materials can be produced by methods analogous to those for known compounds, for example from the corresponding hydroxyl compounds, e.g. by reaction with thionyl chloride or hydrogen chloride or with hydrogen bromide or with methanesulphonyl chloride or p-toluenesulphonyl chloride. Hydroxyl compounds of the general formula II are for their part obtainable for example by the reaction of corresponding 9-phenanthrylmagnesium-bromides with formaldehyde or with ethylene oxide, or by the reduction of corresponding carboxylic acids or carboxylic acid-lower-alkyl esters with diborane or complex hydrides such as lithium aluminium hydride or sodium aluminium-bis-(2-methoxy-ethoxy)-hydride. The 9-phenanthrenecarboxylic acids from which the esters required for the reduction are derived are obtainable in particular by means of the Pschorr synthesis (see Organic Reactions 9, 409–462), whilst corresponding 9-phenanthreneacetic acid esters and 9-phenanthrenepropionic acid esters are obtainable, e.g., from the corresponding 9-(halogenomethyl)-phenanthrenes by reaction with alkali metal cyanides or with sodium-malonic acid-lower-alkyl esters, followed by hydrolysis, if necessary decarboxylation and subsequently esterification [see J. Amer. Chem. Soc. 55, 2955–2959 (1933) and J. Chem. Soc. 1949, 169–173].

Reactive esters of compounds of the general formula II wherein X or Y represents an epithio radical and the reactive esterified hydroxyalkyl group is on the ring B can be produced, for example, by starting with benzo[f]-thieno[2,3-b]thiepin-4-(5H)-one [M. Rajsner et al., Farmaco (Pavia), Ed.Sci. 23, 140–148 (1968)] or benzo[f]-thieno[3,2-b]thiepin-4(5H)-one [see U.S. Pat. No. 3,600,392] or with substituted analogs thereof, such as 2-chlorothieno[2,3-b][1]benzothiepin-4(5H)-one [M. Rajsner et al., Collect. Czech. Chem. Commun. 35, 378–382 (1970), which in their turn are obtainable, for example, by cyclisation of corresponding, optionally substituted, [o-thienyl-phenyl]-acetic acids. If the reactive esterified hydroxyl group is to be in the 4-position, the tricyclic oxo compounds of the above-mentioned type are for example firstly reacted with a methylmagnesium halide to the corresponding 4-hydroxy-4-methyl compounds, and these are dehydrated to give corresponding 4-methyl-benzo[f]thieno[2,3-b]thiepins and 4-methyl-benzo[f]thieno[3,2-b]thiepins. These are converted by splitting off sulphur (sulphur extrusion) analogously to the above-mentioned process (b), preferably by heating with an alkali metal hydroxide in the manner referred to there, into the corresponding 4-methylnaphtho[1,2-b]thiophenes and 4-methyl-naphtho[2,1-b]thiophenes, respectively. By treatment thereof with a suitable halogenating agent, such as N-bromosuccinimide, there are obtained halides, especially bromides, of compounds of the general formula II in which $C_nH_{2n}$ is methylene. In an analogous manner are obtained, e.g. with use of an ethylmagnesium halide in the reaction with a tricyclic oxo compound, halides, particularly bromides, of compounds of the general formula II, in which compounds $C_nH_{2n}$ is ethylidene. The resulting halides, especially bromides, can either be used directly as starting materials or be reacted firstly, e.g., with an alkali metal cyanide or with the sodium compound of a malonic acid- or methylmalonic acid-di-lower-alkyl ester, the resulting nitriles or dicarboxylic acid esters then being hydrolysed and if necessary decarboxylated, the formed, optionally α-methylated, napththo[1,2-b]thiophene- or naphtho [2,1-b]thiophene-4-acetic acids or -4-propionic acids optionally converted into suitable lower alkly esters, and the stated acids or their lower alkyl esters reduced, by means of diborane or of a complex hydride such as lithium aluminum hydride, to the corresponding compounds of the general formula II, i.e., naphtho[1,2-b]thiophene- or naphtho[2,1-b]thiophene-4-ethanols or -4-propanols, in each case optionally substituted as defined and optionally β-methylated. These hydroxyl compounds can be converted in a manner known per se, e.g. by reaction with thionyl chloride, with hydrogen chloride or hydrogen bromide or with a sulphonic acid chloride, such as methanesulphonyl chloride or p-toluenesulphonyl chloride, into the corresponding reactive esters.

For the production of analogous compounds of the general formula II in which the hydroxyalkyl group is in the 5-position, the aforementioned tricyclic oxo compounds are for example firstly methylated, in the manner described in the US Pat. No. 3,682,959 for the production of 5-methyl-thieno [2,3-b][1]benzothiepin-4(5H)-one and 5-methyl-thieno[3,2-b][1] benzothiepin-4(5H)-one, by reaction with a methyl halide in the presence of an alkaline condensation agent, such as sodium amide, in the 5-position. The oxo radical in the 4-position is subsequently reduced to the hydroxyl group, the reduction product is dehydrated to the corresponding 5-methyl-benzo[f] thieno[2,3-b]thiepin or 5-methyl-benzo[f]thieno[3,2-b]thiepin. It is possible to produce in an analogous manner, e.g., also the corresponding 5-ethyl compounds. From here the procedure adopted can be the same as that given above for the 4-methyl compounds, i.e., there now follows the splitting-off of sulphur.

Compounds of the general formula II having an epithio radical as X and an hydroxymethyl group as radical -$C_2H_{2n}$-OH in the 4-position can be obtained, e.g., also by condensation of thiophene-3-acetic acid with a benzaldehyde, optionally substituted as defined, to give the corresponding α-(3-thienyl)-cinnamic acid, cyclisation of this by reaction with oxygen and iodine, with UV irradiation, in ethanol at elevated temperature, and reduction of the resulting naphtho[1,2-b]thiophene-4-acetic acid by means of lithium aluminum hydride.

Compounds of the general formula II in which X is an epithio radical and the hydroxylalkyl group is in the 2-position, i.e., in the ring A, can be produced, in a manner known per se, for example starting with the known corresponding naphtho[1,2-b] thiophene-2-carboxaldehyde and 2-acetyl-naphtho[1,2-b]thiophene [see K. Clarke et al., J. Chem. Soc. 1973, Perkin Transactions I, 2956-2960]. By application of the herein described formylation with N-methylformanilide and phosphoryl chloride or acetylation according to Friedel-Crafts, it is possible to obtain also corresponding compounds having a substituent in the ring B or C. Compounds of the general formula II in which X is an ethylenylene group and the hydroxylalkyl group is in any chosen position in the ring A can be produced, e.g., in a manner known per se from the corresponding aldehydes, i.e., phenanthrene-1-, -2-, -3- or -4-carboxaldehyde.

Of the starting materials of the general formula III, 1H-imidazole and some lower-alkylated 1H-imidazoles, such as the 2,4-dimethyl-, 4,5-dimethyl- and 2,4,5-trimethyl-1H-imidazoles, the 2-ethyl-4(5)-methyl-1H-imidazole, 2-methyl-4(5)-ethyl-1H-imidazole and 4(5)-isobutyl-1H-imidazole, are known, and others are obtainable by methods analogous to those for known compounds, e.g. according to the Weidenhagen synthesis from a lower aliphatic acyloin, a lower aliphatic aldehyde and an amount of ammonia which is at least the double-molar amount, in the presence of the equimolar amount of copper(II)-acetate.

The starting materials of the general formula IV for the process (b) are for their part new substances which are obtainable, for example analogously to process (a), by reaction of reactive esters of corresponding benzo[b]thieno[1,2-b]thiepin-2-, -3-, -4- or -5-alkanols or benzo [b]thieno[2,1-b]thiepin-1-, -2-, -4- or -5-alkanols, or of corresponding phenanthrene derivatives, with compounds of the general formula III. The reactive esters required for this procedure can be obtained, e.g., analogously to those of compounds of the general formula II by means of the aforementioned reaction sequences, with omission of the process step of ring-narrowing sulphur extrusion where this is included in these reaction sequences. A further production possibility for corresponding secondary hydroxyl compounds is the reaction of the aforementioned, in some cases known, tricyclic oxo compounds with metal compounds of alkines, such as alkali metal acetylidene or (2-propynyl)-magnesium halides, and subsequent dehydration with formation of the cyclic double bond; then hydration of the triple bond in the usual manner with the aid of inorganic mercury compounds, and finally reduction or catalytic hydrogenation of the ketones obtained by hydration.

Compounds of the general formula IV in which an optionally lower-alkylated[(1H-imidazol-1-yl)-methyl] group is in the 4-position, and the rings A and C are optionally substituted as defined, can also be obtained for example by condensing an optionally ring-substituted o-(2-thienylthio)-benzaldehyde, which can be produced by methods known per se, firstly by a reaction sequence analogous to that described in US Pat. No. 3,787,444, especially in Example 5, with hippuric acid in the presence of sodium bicarbonate and acetic anhydride at elevated temperature to give correspondingly substituted 2-phenyl-4-[o-(2-thienylthio)-benzylidene]-2-oxazolin-5-one; and then converting this, by a brief boiling in a mixture of acetic acid, water and concentrated sulphuric acid (2:1:1) into optionally correspondingly substituted benzo[f]thieno[2,3-b] thiepin-4-carboxylic acid. This carboxylic acid is thereupon reduced by means of lithium aluminium hydride to the corresponding alcohol, this is converted by means of phosphorus tribromide into the corresponding bromomethyl compound, which is reacted, analogously to process (a), with an optionally lower-alkylated 1H-imidazole or with the sodium compound thereof.

Starting materials of the general formula IV in which the group -$C_nH_{2n}$-Het is bound to the ring A can be produced for example by a procedure completely analogous to that for the corresponding starting materials of the general formula II by using in the first process step for formylation or acetylation, instead of optionally substituted naphtho[1,2]thiophene or naphtho[2,1-b]thiophene, optionally substituted benzo[f]thieno [2,3-b]thiepin or benzo[f]thieno[3,2-b]thiepin.

The starting materials preferably used are those which lead to the groups of compounds of the general formula I or to individual compounds thereof which have been particularly emphasised in the foregoing part of the text.

The present invention relates also to such modifications of the stated processes and to the preliminary stages thereof, wherein a process is interrupted at some stage, or wherein a compound occurring as an intermediate at some stage is used as starting material and the uncompleted steps are performed, or wherein a starting material is formed under the reaction conditions, or, optionally, is used in the form of a salt. If the required starting materials are optically active, then both the racemates and the isolated antipodes can be used, or in the case of diastereometric compoudns either mixtures of racemates or specific racemates, or likewise isolated antipodes, can be used. Furthermore, such starting materials can optionally be used in the form of salts.

If final materials are obtained as racemates or as mixtures of racemates, these can within the scope of the invention be optionally separated and resolved into their antipodes.

The compounds of the general formula I which are obtained by the processes according to the invention are optionally converted, in the customary manner, into their monoacid addition salts with inorganic and organic acids. For example, salts are formed with the acids mentioned hereinbefore, and with other acids, in the presence of a solvent such as acetone, methanol, ethanol or ether, or mixtures thereof. Pharmaceutically acceptable acid addition salts are preferably produced, but other acid addition salts can be of importance if, for example, they crystallise well and are therefore suitable for separation, purification and, optionally, storage of the reaction products finally used as free bases or in the form of other then pharmaceutically acceptable, acid addition salts.

The compounds of the general formula I and their monoacid pharmaceutically acceptable acid addition salts are preferably administered orally or rectally; they can however also be administered parenterally in the form of aqueous solutions of their acid addition salts.

The daily doses for enternal or parenteral administration to warmblodded animals vary between 0.10 and 10 mg/kg, and for larger warmblooded animals of about 70 kg body weight they are preferably between 10 and 100 mg/kg. Suitable dosage units, such as dragees, tablets or suppositories, preferably contain 2.5 to 100 mg of an active substance according to the invention, i.e., of a compound of the general formula I, or of a pharmaceutically acceptable acid addition salt of such a compound. Customary pharmaceutical compositions, in particular dosage units, are produced by combining the active substance with at least one pharmaceutical excipient, e.g., with solid pulverulent carriers such as lactose, saccharose, sorbitol, or mannitol; starches such as potato starch, maize starch or amylopectin, also laminaria powder or citrus pulp powder; cellulose derivatives or gelatine, optionally with the addition of lubricants, such as magnesium or calcium stearate or polyethylene glycols, to form tablets or dragee cores. The dragee cores are coated, for example, with concentrated sugar solutions which can also contain, e.g., gum arabic, talcum and/or titanium dioxide, or with a lacquer dissolved in readily volatile organic solvents or solvent mixtures. Dyestuffs may be added to these coatings, e.g. for identification of the various dosage amounts. Further suitable oral dosage units are hard gelatine capsules, and soft closed capsules made from gelatine and a softener such as glycerin. The hard gelatine capsules contain the active substance preferably as a granulate in admixture with lubricants, such as talcum or magnesium stearate, and optionally stabilisers such as sodium metabisulphite or ascorbic acid.

The following working examples further illustrate the production of tablets, dragees, suppositories and ampoules:

(a) 250.0 g of 1-[(naphtho[1,2-b]thien-4-yl)-methyl]-1H-imidazole-methanesulphonate is mixed with 500 g of lactose and 292 g of potato starch; the mixture is moistened with an alcoholic solution of 8 g of gelatine, and then granulated through a sieve. After drying of the granulate, 60 g of potato starch, 60 g of talcum, 10 g of magnesium stearate and 20 g of highly-dispersed silicon dioxide are mixed in, and the mixture is pressed out to form 10,000 tablets each weighing 120 mg and each containing 25 mg of active substance; the tablets can be provided with grooves to effect a more precise adjustment of the dosage amount.

(b) 12.5 g of 1-[(naphtho[1,2-b]thien-4-yl)-methyl]-1H-imidazole-methanesulphonate is well mixed with 16 g of maize starch and 6 g of highly dispersed silicon dioxide. The mixture is moistened with a solution of 2 g of stearic acid, 6 g of ethylcellulose and 6 g of stearin in about 70 ml of isopropyl alcohol, and is then granulated through a sieve having a mesh size of 1.2 mm. The granulate is dried for about 14 hours and is subsequently put through a sieve having a mesh size of 1.2 to 1.5 mm. It is then mixed with 16 g of maize starch, 16 g of talcum and 2 g of magnesium stearate, and the mixture is pressed out to form 1000 dragee cores. These are coated with a concentrated syrup of 2 g of lacca, 7.5 g of gum arabic, 0.15 g of dyestuff, 2 g of highly dispersed silicon dioxide, 25 g of talcum and 53.35 g of sugar, and finally dried. The dragees obtained each weigh 172.5 mg and each contain 12.5 mg of active substance.

(c) 25.0 g of 1-[(naphtho[1,2-b]thien-4-yl)-methyl]-1H-imidazole-methanesulphonate and 1975 g of finely ground suppository foundation substance (e.g. cocoa butter) are thoroughly mixed and then melted. From the melt, maintained homogeneous by stirring, are formed 1000 suppositories each weighing 2 g and each containing 25 mg of active substance.

(d) 25.0 g of 1-[(naphtho[1,2-b]thien-4-yl)-methyl-1H-imidazole-methanesulphonate is dissolved in 1 liter of bi-distilled pyrogen-free water, and the solution is filled into 1000 ampoules and sterilised. An ampoule contains a 2.5% solution of 25 mg of active substance.

The following Examples further illustrate the production of the new compounds of the general formula I and of starting materials not hitherto known, but they are not intended to limit in any way the scope of the invention. The temperature values are given in degrees Centigrade.

EXAMPLE 1

27.7 g (0.1 mole) of 4-(bromomethyl)-naphtho[1,2-b]thiophene is dissolved in 180 ml of benzene, and the solution is added dropwise at 40° within one hour, with stirring, to a solution of 40.8 g (0.6 mole) of 1H-imidazole in 400 ml of benzene and 50 ml of methanol. The reaction mixture is stirred for a further two hours at 70°–80°; it is then cooled and 200 ml of water is added. The organic phase is separated in a separating funnel from the aqueous phase, repeatedly washed with water, dried over potassium carbonate and concentrated by evaporation. To the oily residue is added 100 ml of ether, whereupon 1-(naphtho [1,2-b]thien-4-yl)-methyl]-1H-imidazole crystallises out, m.p. 110°–111°.

For conversion into the methanesulphonate, the free base is dissolved in acetone, and the theoretical amount of methanesulphonic acid is added, whereupon 1-[(naphtho[1,2-b]thien-4-yl)-methyl]-1H-imidazole-methanesulphonate crystallises out, m.p. 150°–151°.

The starting material can be produced in the following manner:

(a) A solution of 116 g (0.5 mole) of benzo[f]thieno[2,3-b]thiepin-4(5H)-one [(M. Rajsner et al., Farmaco (Pavia), Ed. Sci. 23, 140–148, (1968)] in 690 ml of absolute benzene is added dropwise in the course of one hour, with thorough stirring, to a Grignard solution prepared from 24.5 g (1.0 mole) of magnesium, 225 ml of abs. ether and 142 g (1.0 mole) of methyl iodide, with a reaction temperature of −5° to 0° being maintained. The reaction mixture is subsequently heated to 45° and is stirred at this temperature for a further 15 hours. The reaction mixture is then cooled to 0° and is stirred into a solution of 340 g of ammonium chloride in 1000 ml of ice water. The organic phase is separated, and the aqueous phase is extracted with benzene. The combined organic solutions are washed with water, dried over sodium sulphate and concentrated in vacuo to leave as residue 4-methyl-4,5-dihydrobenzene[f]thieno[2,2-b]thiepin-4-ol (crude product) in the form of yellow oil.

(b) 124 g (0.5 mole) of crude 4-methyl-4,5-dihydro-benzo[f] thieno[2,3-b]thiepin-4-ol in 640 ml of 2 N sulphuric acid is refluxed with stirring for 5 hours. The mixture is then cooled to 20° and extracted with ether; the organic phase is washed with water, dried over potassium carbonate and concentrated by evaporation. The residue is dissolved in 620 ml of abs. ethanol; to this solution is then added 124 g of potassium hydroxide, and the mixture is subsquently refluxed for 5 hours. The reaction mixture is thereupon poured into water and extracted with ether. The organic phase is washed with water, dried over potassium carbonate and concentrated by evaporation. The residue, 4-methyl-benzo[f]thieno[2,3-b]thiepin, melts at 65–67° fter recrystallisation from ether/petroleum ether.

(c) 115 g (0.5 mole) of 4-methyl-benzo[f]thieno[2,3-b]thiepin, 980 ml of ethylene glycol and 100 g of potassium hydroxide are refluxed for 9 hours with stirring and in a nitrogen atmosphere. The mixture is thereupon cooled to 20°, diluted with 800 ml of water and extracted with petroleum ether. The organic phase is separated, washed with water, dried over sodium sulphate and concentrated by evaporation. The residue is distilled under high vacuum, b.p. 109°–116°/0.01 Torr. On cooling there crystallises 4-methyl-naphtho[1,2-b]thiophene, m.p. 32–33°.

(d) 99 g (0.5 mole) of 4-methyl-naphtho[1,2-b]thiophene is dissolved in 990 ml of carbon tetrachloride, and to the solution is added 89 g (0.5 mole) of N-bromosuccinimide. The mixture is heated to boiling, with stirring and in a nitrogen atmosphere, whilst being irradiated with a UV lamp. The mixture is kept boiling until all the N-bromosuccinimide, which is lying on the bottom of the vessel, has been converted to succinimide floating on the surface of the solution; the duration is about 15 minutes. The reaction mixture is thereupon cooled to 20°, and the succinimide is separated by filtration. The filtrate is washed with water, dried over sodium sulphate and concentrated by evaporation. On cooling there crystallises 4-(bromomethyl)-naphtho[1,2-b]thiepin, m.p. 107–110°.

EXAMPLE 2

Analogously to Example 1 is obtained, from 30.6 g (0.1 mole) of 4-[(2-methylsulphonyloxy)-ethyl]-naphtho[1,2-b]thiophen and 40.8 g (0.6 mole) of 1H-imidazole in benzene/methanol, 1-[2-(naphtho[1,2-b]thien-4-yl)-ethyl]-1H-imidazole as crude product. For conversion into the hydrochloride, the crude base is dissolved in acetone, this solution is neutralised with the theoretical amount of a 4 N absolute-ethanolic hydrochloric acid, and abs. ether is added until a slight clouding occurs, whereupon 1-[2-(naphtho[1,2-b]thien-4-yl)-ethyl]-1N-imidazole hydrochloride, m.p. 120–130°, crystallises out.

The starting material can be produced in the following manner:

(a) 27.7 g (0.1 mole) of 4-(bromomethyl)-naphtho[1,2-b]thiophene is dissolved at 50°, with stirring in a nitrogen atmosphere, in 900 ml of acetonitrile. To this solution is added dropwise within 10 minutes a solution of 5.9 g (0.12 mole) of sodium cyanide in 36 ml of water, and the mixture is subsequently stirred at 50° for a further 3 hours. The reaction mixture is then concentrated in vacuo, and water is added to the residue, whereupon naphtho[1,2-b]thiophene-4-acetonitrile crystallises out: this melts at 122–125° after recrystallisation from acetonitrile.

(b) 22.3 g (0.1 mole) of naphtho[1,2-b]thiophene-4-acetonitrile, 220 ml of ethanol and 22 ml of 50% potassium hydroxide solution are refluxed with stirring in a nitrogen atmosphere for 20 hours. The reaction mixture is subsequently cooled, dissolved in 900 ml of water and filtered, and the filtrate is made acid to a congored indicator with conc. hydrochloric acid, with naphtho[1,2-b]thiophene-4-acetic acid, m.p. 193–195°, crystallising out.

(c) 24.2 g (0.1 mole) of naphtho[1,2-b]thiophene-4-acetic acid, 170 ml of benzene, 8 g of abs. ethanol and 1.4 ml of conc. sulphuric acid are refluxed with stirring for 20 hours on a water separator. The reaction mixture is subsequently cooled, washed with water and 2 N sodium carbonate solution, dried over sodium sulphate and highly concentrated in vacuo. To the concentrated solution is added petroleum ether, whereupon naphtho[1,2-b]thiophene-4-acetic acid ethyl ester, m.p. 59°–60°, crystallises out.

(d) A solution of 27 g (0.1 mole) of naphtho[1,2-b]thiophene-4-acetic acid ethyl ester in 120 ml of ether is added dropwise within one hour, with stirring in a nitrogen atmosphere, to a suspension of 5.7 g (0.15 mole) of lithium aluminium hydride in 150 ml of ether, with the temperature being maintained at 20°–30°. The reaction mixture is subsequently refluxed for 15 hours and then cooled to 0°–5°. The unreacted lithium aluminium hydride is decomposed by the careful dropwise addition of 35 ml of ethyl acetate and then of 60 ml of water. The organic phase is subsequently separated, repeatedly washed with water, dried over sodium sulphate and concentrated by evaporation. There is added to the concentrated solution petroleum ether, whereupon naphtho[1,2-b]thiophene-4-ethanol, m.p. 84°–85°, crystallises out.

(e) 8.4 ml (0.11 mole) of methanesulphonyl chloride is added dropwise within 15 minutes, at a reaction temperature of 20°–25°, to a solution of 22.8 g (0.1 mole) of naphtho[1,2-b]thiophene-4-ethanol, 120 ml of anhydrous methylene chloride and 60 ml of pyridine. The reaction mixture is subsequently allowed to stand for 16 hours at room temperature; it is then concentrated in vacuo, and to the residue is added 200 ml of water, whereupon 4-[2-(methylsulphonyloxy)-ethyl]naphtho[1,2-b]thiophene, m.p. 114°–116°, crystallises out.

EXAMPLE 3

Analogously to Example 1 there is obtained, from 27.7 g (0.1 mole) of 4-(bromomethyl)-naphtho[2,1-b]thiophene and 40.8 g (0.6 mole) of 1H-imidazole in benzene/methanol, 1-[(naphtho[2,1-b]thien-4-yl)methyl]-1H-imidazole as crude product, and from that is obtained methanesulphonate, m.p. 170°–173° (from abs. ethanol).

The starting material can be produced analogously to Examples 1(a) to (d):

(a) From 4.9 g (0.2 mole) of magnesium and 28.4 g (0.2 mole) of methyl iodide in abs. ether and 23.2 g (0.1 mole) of benzo[f]thieno[3,2-b]thiepin-4(5H)-one (J. R. Geigy A. G., Belgian Patent No. 715,362 and U.S. Pat. No. 3,600,392) is abs. benzene is obtained 4-methyl-4,5-dihydro-benzo[f]thieno [3,2-b]thiepin-4-ol, m.p. 111°–113° (from methanol).

(b) From 24.8 g (0.1 mole) of 4-methyl-4,5-dihydro-benzo[f]thieno[3,2-b]thiepin-4-ol is obtained, with use firstly of 125 ml of 2 N sulphuric acid and secondly of 110 ml of 20% abs. ethanolic potassium hydroxide solution, 4-methyl-benzo[f]thieno [3,2-b]thiepin, m.p. 89°–91° (from ethanol/water).

(c) From 23 g of 4-methyl-benzo[f]thieno[3,2-b]thiepin, 196 ml of ethylene glycol and 20 g of potassium hydroxide is obtained 4-methyl-naphtho[2,1-b]thiophene, m.p. 72°–75° (from acetonitrile).

(d) From 19.8 g (0.1 mole) of 4-methyl-naphtho[2,1-b]thiophene, 17.8 g (0.1 mole) of N-bromosuccinimide and 178 ml of carbon tetrachloride is obtained 4-(bromomethyl)-naphtho[2,1-b]thiophene, m.p. 151°–154° (from carbon tetrachloride).

EXAMPLE 4

Analogously to Example 1 is obtained, from 27.7 g (0.1 mole) of 5-(bromomethyl)-naphtho[1,2-b]thiophene and 40.8 g (0.6 mole) of 1H-imidazole in 200 ml of benzene/methanol 4:1, 1-[(naphtho[1,2-b]thien-5-yl)-methyl]-1H-imidazole, m.p. 145°–147°; hydrochloride m.p. 223°–224°.

The starting material can be produced as follows:

(a) 24.6 g (0.1 mole) of 5-methyl-benzo[f]thieno[2,3-b]thiepin-4(5H)-one [see British Patent No. 1,334,538 and U.S. Pat. No. 3,682,959) is suspended in 350 ml of abs. ethanol, and to the suspension is added at 8°, with stirring, 3.8 g (0.1 mole) of sodium borohydride. The mixture is then stirred for 15 hours at room temperature. The clear solution is concentrated in vacuo, and the oily residue is taken up in methylene chloride. The solution is washed twice with water, dried over sodium sulphate and concentrated by evaporation, and the residue is dried in vacuo. The 4,5-dihydro-5-methyl-benzo[f]thieno[2,3-b]thiepin-4-ol thus obtained is a white, slightly sticky, solid mass, and is further processed as crude product.

(b) 24.8 g (0.1 mole) of 4,5-dihydro-5-methyl-benzo[f]thieno [2,3-b]thiepin-4-ol in 600 ml of benzene is boiled, with the addition of 0.57 g (0.03 mole) of p-toluenesulphonic acid hydrate, for one hour on a water separator. The solution is thereupon cooled to 20°, extracted by shaking with 2 N sodium bicarbonate solution, dried over sodium sulphate and concentrated in vacuo. The oily residue is chromatographed on a silica-gel column (300 g of silica gel, particle size 0.063-0.2 mm) with the use of cyclohexane as the eluant. Recrystallisation of the eluted substance from pentane yields 5-methyl-benzo[f]thieno[2,3-b]thiepin, m.p. 70°-71°.

(c) Analogously to Example 1(c) is obtained 5-methyl-naphtho[1,2-b]thiophene as colourless oil, b.p. 110°/0.03 Torr, starting with 23 g (0.1 mole) of 5-methyl-benzo[f]thieno[2,3-b]thiepin, 200 ml of ethylene glycol and 20 g of potassium hydroxide.

(d) Analogously to Example 1(d) is obtained 5-(bromomethyl)-naphtho[1,2-b]thiophene, m.p. 99°-101°, starting with 19.8 g (0.1 mole) of 5-methyl-naphtho[1,2-b]thiophene in 200 ml of carbon tetrachloride and 17.8 g (0.1 mole) of N-bromosuccinimide.

EXAMPLE 5

Analogously to Example 1 are obtained, from 27.1 g (0.1 mole) of 9-(bromomethyl)-phenanthrene and 40.8 g (0.6 mole) of 1H-imidazole in benzene/methanol, 1-[(9-phenanthrenyl)-methyl]-1H-imidazole, m.p. 122°-123° (from toluene), and its (1:1)-maleate, m.p. 156°-158° (from abs. ethanol/abs. ether).

The starting material is produced analogously to Example 1(d) with use of 33.6 g (0.2 mole) of 9-methyl-phenanthrene [see N. D. Zelinsky et al., Ber. 61, (1928)] and 36 g (0.2 mole) of N-bromosuccinimide in 400 ml of carbon tetrachloride.

EXAMPLE 6

Analogously to Example 1 are obtained, from 27.7 g (0.1 mole) of 4-(bromomethyl)-naphtho[1,2-b]thiophene and 49.2 g (0.6 mole) of 2methyl-1H-imidazole in benzene/methanol, 1-[(naphtho[1,2-b]thien-4-yl)-methyl]-2-methyl-1H-imidazole, m.p. 123°-124° (from acetone), and its methanesulphonate, m.p. 190°-191° (from abs. ethanol).

EXAMPLE 7

29.6 g (0.1 mole) of 1-[(benzo[f]thieno[2,3-b]thiepin-4-yl)-methyl]-1H-imidazole, 230 ml of ethylene glycol and 20 g of potassium hydroxide are refluxed with stirring in a nitrogen atmosphere for 3 hours. The reaction mixture is then cooled to 20°, and 500 ml of water is added, whereupon 1-[(naphtho[1,2-b]thiophen-4-yl)-methyl]-1H-imidazole, m.p. 109°-111°, crystallises.

The starting material is produced as follows:

(a) 115 g (0.5 mole) of 4methyl-benzo[f]thieno[2,3-b]thiepin [see Example 1(a) and (b)]is dissolved in 1150 ml of carbon tetrachloride, and to the solution is added 89 g (0.5 mole) of N-bromosuccinimide. The mixture is heated to boiling, with stirring in a nitrogen atmosphere, whilst being irradiated with a UV lamp. The mixture is kept at the boil until all the N-bromosuccinimide has been converted into succinimide floating on the surface of the solution; the time for this is about one hour. The reaction mixture is thereupon cooled to 20°, and the succinimide is filtered off. The filtrate is washed with water, dried over sodium sulphate and concentrated in vacuo. The oily residue is dissolved in ether, and the solution is cooled to 0°, whereupon 4-(bromomethyl)-benzo[f]thieno[2,3-b]thiepin, m.p. 90°-92°, crystallises out.

(b) 30.9 g (0.1 mole) of 4-(bromomethyl)-benzo[f]thieno[2,3-b]thiepin is dissolved in 180 ml of benzene, and the solution is added dropwise at 45° within one hour, with stirring, to a solution of 40.8 g (0.6 mole) of 1H-imidazole in 400 ml of benzene and 50 ml of methanol. The reaction mixture is stirred for a further hour at 60°-65° and then cooled; and 200 ml of water is subsequently added. The organic phase is separated in a separating funnel from the aqueous phase, repeatedly washed with water, dried over potassium carbonate and concentrated by evaporation. The crystalline residue, 1-[(benzo[f]thieno[2,3-b]thiepin-4-yl)-methyl]-1H-imidazole, melts at 174°-175° after recrystallisation from acetone.

EXAMPLE 8

By a procedure analogous to that of Example 1 there are obtained, from 29.1 g (0.1 mole) of 4-(1-bromoethyl)-naphtho [1,2-b]thiophene and 40.8 g (0.6 mole) of 1H-imidazole in benzene/methanol, 1-[1-(naphtho[1,2-b]thien-4-yl)-ethyl]-1H-imidazole, m.p. 114°-115° (from toluene), and its hydrochloride, m.p. 232°-234° (from abs. ethanol).

The starting material is produced analogously to Examples 1(a) to 1(d):

(a) From 4.9 g (0.2 mole) of magnesium, 31.2 g (0.2 mole) of ethyl iodide in abs. ether and 23.2 g (0.1 mole) of benzo[f]thieno[2,3-b]thiepin-4(5H)-one, there is obtained 4-ethyl-4,5-dihydro-benzo[f]thieno[2,3-b]thiepin-4-ol as an oily crude product.

(b) From 26.2 g (0.1 mole) of 4-ethyl-4,5-dihydro-benzo[f]thieno[2,3-b]thiepin-4-ol, there is obtained, with use firstly of 125 ml of 2 N sulphuric acid and secondly of 110 ml of 20% abs. ethanolic potassium hydroxide solution, 4-ethyl-benzo[f]thieno[2,3-b]thiepin, b.p. 125°-128°/0.1 Torr.

(c) From 24.4 g (0.1 mole) of 4-ethyl-benzo[f]thieno[2,3-b]thiepin, 196 ml of ethylene glycol and 20 g of potassium hydroxide, there is obtained 4-ethyl-naphtho[1,2-b]thiophene, b.p. 114°-118°/0.1 Torr.

(d) From 21.2 g (0.1 mole) of 4-ethyl-naphtho[1,2-b]thiophene, 17.8 g of N-bromosuccinimide and 178 ml of carbon tetrachloride, there is obtained 4-[1-bromoethyl]-naphtho[1,2-b]thiophene, m.p. 94°-95° (from carbon tetrachloride).

EXAMPLE 9

By a procedure analogous to that of Example 1, there is obtained, from 27.7 g (0.1 mole) of 2-(bromomethyl)-naphtho [1,2-b]thiophene and 40.8 g (0.6 mole) of 1H-imidazole in benzene/methanol, 1-[(naphtho[1,2-b]thien-2-yl)-methyl]-1H-imidazole, m.p. 121°-123° (from benzene); methanesulphonate, m.p. 164°–166° (from abs. ethanol).

The starting material is produced as follows:

(a) 21.2 g (0.1 mole) of naphtho[1,2-b]thiophene-2-carboxaldehyde is suspended in 445 ml of absolute ethanol, and to the suspension is added at 10°, with stirring, 3.8 g (0.1 mole) of sodium borohydride. The mixture is subsequently stirred at room temperature for a further 3 hours. The reaction mixture is then diluted with 1250 ml of water, whereupon naphtho[1,2-b]thiophene-2-methanol crystallises out. After filtration under suction and drying in vacuo at 60°, the product is recrystallised from hexane, m.p. 88°–89°.

(b) A solution of 10.8 g (0.04 mole) of phosphorus tribromide in 150 ml of chloroform is added dropwise at 5° within 45 minutes, with stirring, to a suspension of 21.4 g (0.1 mole) of naphtho [1,2-b]thiophene-2-methanol in 110 ml of chloroform, with the gradual formation of a solution. The reaction mixture is stirred for a further 5 hours at 5°, and ice water is subsequently added. The organic phase is separated, washed twice with water and, after drying over sodium sulphate, concentrated at a maximum of 40° in vacuo. The 2-(bromomethyl)-naphtho[1,2-b] thiophene obtained as residue crystallises on addition of diethyl ether, and melts at 75°–78°.

EXAMPLE 10

By a procedure analogous to that given in Example 1, there is obtained, from 29.1 g (0.1 mole) of 2-(1-bromoethyl) naphtho[1,2-b]thiophene and 40.8 g (0.6 mole) of 1H-imidazole in benzene/methanol, 1-[1-(naphtho[1,2-b]thien-2-yl)-ethyl]-1H-imidazole, crude product (oil); hydrochloride m.p. 214°–216° (from abs. ethanol).

The starting material is produced as follows:

(a) A solution of 21.2 g (0.1 mole) of naphtho[1,2-b]thiophene-2-carboxaldehyde in 50 ml of abs. toluene is added dropwise in the course of one hour, with stirring, to a Grignard solution prepared from 2.94 g (0.12 mole) of magnesium, 40 ml of abs. ether and 15.9 g (0.12 mole) of methyl iodide, with a reaction temperature of 10°–15° being maintained. The reaction mixture is subsequently heated to 50°, and is stirred for 14 hours at this temperature. The reaction mixture is then cooled to 0°, and is stirred into a solution of 40 g of ammonium chloride in 140 ml of ice water. The organic phase is separated, and the aqueous phase is extracted with ether. The combined organic solutions are washed with water, dried over sodium sulphate and concentrated in vacuo. The residue is dissolved in a small amount of petroleum ether, whereupon α-methyl-naphtho[1,2-b]thiophene-2-methanol, m.p. 54°–55°, crystallises out.

(b) 2-(1-Bromoethyl)-naphtho[1,2-b]thiophene, m.p. 104°–107° (from diethyl) is obtained, analogously to Example 10(b), from 22.8 g (0.1 mole) of α-methyl-naphtho[1,2-b]thiophene-2-methanol and 10.8 g (0.04 mole) of phosphorus tribromide in chloroform.

EXAMPLE 11

1-[(8-chloro-naphtho[1,2-b]thien-4-yl)-methyl]-1H-imidazole-methanesulphonate, m.p. 197°–198°, is obtained, by a procedure analogous to that of Example 1, from 31.1 g (0.1 mole) of 4-(bromomethyl)8-chloro-naphtho[1,2-b]thiophene and 40.8 g (0.6 mole) of 1H-imidazole in 200 ml of benzene/methanol 4:1.

The starting material can be produced as follows:

(a) A mixture of 14.2 g (0.1 mole) of 3-thiophenacetic acid, 14.0 g (0.1 mole) of p-chlorobenzaldehyde, 10 ml of triethylamine and 20 ml of acetic anhydride is refluxed under nitrogen for 5 hours. After cooling, the dark-brown reaction product is taken up in methylene chloride, and the acid constituents are extracted by shaking with 2 N sodium hydroxide solution.

The alkaline extracts are combined, and the pH value brought to 3 with 2 N hydrochloric acid, whereupon p-chloro-α-(3-thienyl)-cinnamic acid precipitates. This is filtered off with suction and recrystallised from toluene, m.p. 206°–207°.

(b) A solution of 2.65 g (0.01 mole) of p-chloro-α-(3-thienyl)-cinnamic acid and 0.2 g of iodine in 1500 ml of ethanol is irradiated with a low-pressure UV lamp, with stirring and the introduction of air, for 30 hours at room temperature. The reaction mixture is subsequently concentrated in a water-jet vacuum to a volume of about 100 ml. The 8-chloro-naphtho[1,2-b]thiophene-4-carboxylic acid which has precipitated is filtered off with suction, m.p. 300°–305°.

(c) 2.63 g (0.01 mole) of 8-chloro-naphtho[1,2-b]thiophene-4-carboxylic acid is added portionwise at 0°, with stirring and under nitrogen, to a suspension of 0.78 g (0.02 mole) of lithium aluminium hydride in 100 ml of abs. tetrahydrofuran. The reaction mixture is subsequently stirred for 15 hours at room temperature. For processing, there is added to the reaction mixture 15 ml of tetrahydrofuran/water 4:1; the precipitate resulting is filtered off, and the filtrate is concentrated in a water-jet vacuum, whereupon 8-chloro-naphtho[1,2-b]thiophene-4-methanol crystallises out, m.p. 181°–182°.

(d) By a procedure analogous to that given in Example 9(b), there is obtained 4-bromomethyl-8-chloro-naphtho[1,2-b]thiophene, m.p. 144°–146°, starting with 2.49 g (0.01 mole) of 8-chloro-naphtho[1,2-b]thiophene-4-methanol in 20 ml of carbon tetrachloride and 1.2 g (0.044 mole) of phosphorus tribromide.

EXAMPLE 12

13.6 g (0.2 mole) of 1H-imidazole is dissolved in 200 ml of absolute tetrahydrofuran, and to the solution is added portionwise with stirring, in a nitrogen atmosphere, 2.3 g (0.1 gram atom) of sodium, with slight self-heating occurring accompanied by the evolution of hydrogen. The reaction mixture is heated at 45°–50° until the sodium has been completely absorbed. There is subsequently added dropwise at the same temperature, within 60 minutes, a solution of 27.7 g (0.1 mole) of 4-(bromomethyl)-naphtho[1,2-b]thiophene in 50 ml of tetrahydrofuran, and stirring is continued at 45°–50° for a further two hours. After cooling, the sodium bromide which has precipitated is filtered off, and the filtrate is concentrated in a water-jet vacuum. The residue is taken up in 400 ml of ether and 200 ml of water. The organic phase is separated in a separating funnel from the aqueous phase, washed repeatedly with water, dried over sodium sulphate and concentrated in a water-jet vacuum to leave as residue 1-[(naphtho[1,2-b]thiophen-4-yl)-methyl]-1H-imidazole, m.p. 109°–111°.

EXAMPLE 13

By a procedure analogous to that of Example 7, there are obtained 1-[(7-chloro-naphtho[1,2-b]thien-4-yl)-methyl]-1H-imidazole, m.p. 150°–152°, and its hydrochloride, m.p. 260°–261°, from 33.1 g (0.1 mole) of 1-[(7-chloro-benzo[f]thieno[2,3-b]thiepin-4-yl)-methyl]-1H-imidazole, 230 ml of ethylene glycol and 20 g of potassium hydroxide.

The starting material can be produced as follows:

(a) To 30 ml of abs. ether cooled to 3° is added under nitrogen 1.14 g (0.03 mole) of lithium aluminium hydride, and there is then added dropwise at 5°–10° with stirring, within half an hour, a solution of 5.4 g (0.02 mole) of 5-chloro-2-(2-thienylthio)-benzoic acid (produced according to Swiss Patent Specification No. 405,354; C.A. 66, P 2550e) in 45 ml of abs. ether. After completion of the dropwise addition, the mixture is refluxed for 16 hours; and there is thereupon slowly added dropwise at 3°–7° 5 ml of water. The occurring precipitate is filtered off with suction, and subsequently well washed with ether. The filtrate is concentrated in vacuo, and the residue is recrystallised from carbon tetrachloride to yield 5-chloro-2-(2-thienylthio)-benzyl alcohol having a melting point of 95°–96°.

(b) To a solution of 51.4 g (0.2 mole) of 5-chloro-2-(2-thienylthio)-benzyl alcohol in 400 ml of toluene is added 173.9 g (2.0 mole) of manganese (IV)-oxide, and stirring is maintained at 20°–25° for 25 hours. The precipitate is then filtered off with suction, and the filtrate is concentrated in vacuo to yield 5-chloro-2-(2-thienylthio)-benzaldehyde as yellow oil.

(c) 8.4 g (0.1 mole) of sodium bicarbonate is added, with stirring, to the mixture of 25.5 g (0.1 mole) of 5-chloro-2-(2-thienylthio)-benzaldehyde and 17.9 g (0.1 mole) of hippuric acid in 34.7 g (0.34 mole) of acetic anhydride, and the reaction mixture is stirred at 90°–95° for two hours. It is thereupon cooled to 25°; to the thick crystal mass is added 300 ml of 50% ethanol, the solid substance is filtered off with suction and is washed with 150 ml of 50% ethanol. Drying in a vacuum chamber leaves 2-phenyl-4-[5-chloro-2-(2-thienylthio)-benzylidene]-2-oxazolin-5-one in the form of yellow crystals, m.p. 125°–127°.

(d) 4.0 g (0.01 mole) of 2-phenyl-4-[5-chloro-2-(2-thienylthio)-benzylidene]-2-oxazolin-5-one in 175 ml of an acid mixture consisting of glacial acetic acid, water and 96% sulphuric acid in the volume ratio of 2:1:1 is heated to boiling for 20 minutes with stirring and under nitrogen. There is then added dropwise at 5° 100 ml of water; the violet precipitate is filtered off with suction, and the residue is thoroughly washed with water. The crude product thus obtained is dissolved in 250 ml of ether, and the ether solution is extracted twice with 100 ml of 0.1 N sodium hydroxide solution each time. The combined extracts are adjusted with dilute hydrochloric acid to have a pH value of 3; the substance which has precipitated is then filtered off with suction and dried in a vacuum chamber to thus yield 7-chlorobenzo[f]thieno[2,3-b]thiepin-4-carboxylic acid, m.p. 295°–300°.

(e) To 40 ml of abs. ether is added at 3° under nitrogen 0.76 g (0.02 mole) of lithium aluminium hydride, and there is then added dropwise at 5° with stirring, in the course of half an hour, a solution of 2.9 g (0.01 mole) of 7-chlorobenzo[f]thieno [2,3-b]thiepin-4-carboxylic acid in 60 ml of abs. ether and 20 ml of abs. tetrahydrofuran. The mixture is subsequently stirred for 2 hours at room temperature; 4 ml of water is then slowly added dropwise at 5°, and the precipitate is filtered off with suction. The filtrate is concentrated in vacuo; the crude residue is chromatographed on a silica-gel column, and by elution with chloroform is yielded 7-chlorobenzo[f]thieno[2,3-b]thiepin-4-methanol, m.p. 117°–120°.

(f) In a manner analogous to that of Example 9(b) is produced 4-(bromomethyl)-7-chlorobenzo[f]thieno[2,3-b]thiepin in the form of oily crystals, starting with 2.8 g (0.01 mole) of 7-chlorobenzo[f]thieno[2,3-b]thiepin-4-methanol, 20 ml of carbon tetrachloride and 1.2 g (0.0044 mole) of phosphorus tribromide.

(g) In a manner analogous to that of Example 7(b) is produced 1-[(7-chlorobenzo[f]thieno[2,3-b]thiepin-4-yl)-methyl]-1H-imidazole, m.p. 154°–156°, starting with 3.44 g (0.01 mole) of 4-(bromomethyl)-7-chlorobenzo[f]thieno[2,3-b]thiepin and 4.1 g (0.06 mole) of 1H-imidazole in 40 ml of benzene and 5 ml of methanol.

What we claim is:

1. An imidazole derivative of the formula I

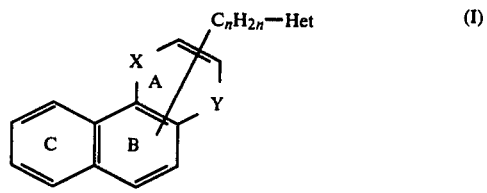

wherein
Het represents 1H-imidazol-1-yl which is unsubstituted or is substituted by lower alkyl,
one of the symbols X and Y represents the epithio radical -S- and the other represents the direct bond, and
n represents 1 to 4, and
besides the substitution of ring A or B by the radical-$C_nH_{2n}$-Het, ring A is unsubstituted or is monosubstituted by chlorine or methyl, ring B is unsubstituted or is monosubstituted by chlorine, methyl or methoxy, and ring C is unsubstituted or is monosubstituted by halogen up to atomic number 35, trifluoromethyl, lower alkyl, lower alkoxy or lower alkylthio; and the pharmaceutically acceptable monoacid acid addition salts thereof.

2. A compound according to claim 1 corresponding to the formula I given in claim 1, in which the radical -$C_nH_{2n}$-Het is bound to the ring B and Het, X, Y and n have the meanings defined in claim 1 and the rings A, B and C are unsubstituted or substituted as defined in claim 1, and the pharmaceutically acceptable monoacid acid addition salts thereof.

3. A compound according to claim 1, corresponding to the formula I given in claim 1, in which Het represents 1H-imidazol-1-yl which is unsubstituted or is substituted by methyl, and n is 1 or 2, X and Y have the meanings given in claim 1, the rings A and B, besides being substituted by the radical -$C_nH_{2n}$-Het, are not substituted, and ring C is unsubstituted or is monosubstituted by halogen up to atomic number 35, trifluoromethyl, lower alkyl, lower alkoxy or lower alkylthio; and the pharmaceutically acceptable monoacid acid addition salts thereof.

4. A compound according to claim 1, corresponding to the formula I given in claim 1, in which Het represents 1H-imidazol-1-yl which is unsubstituted or is substituted by methyl, and n is 1 or 2, X and Y have the meanings given in claim 1, the ring A is not substituted, the radical -$C_nH_{2n}$-Het is bound to the ring B and this ring is not further substituted, and ring C is unsubstituted or is monosubstituted by halogen up to atomic number 35, trifluoromethyl, lower alkyl, lower alkoxy or lower alkylthio; and the pharmaceutically acceptable monoacid acid addition salts thereof.

5. A compound according to claim 1, corresponding to the formula I given in claim 1, in which Het represents unsubstituted 1H-imidazol-1yl, n represents 1, and one of the symbols X and Y represents epithio and the other the direct bond, the rings A and B, besides being substituted by the radical -C$_n$H$_{2n}$-Het, are not substituted, and the ring C is unsubstituted or is monosubstituted by chlorine; and the pharmaceutically acceptable monoacid acid addition salts thereof.

6. A compound according to claim 1 corresponding to the formula I given in claim 1, in which Het represents unsubstituted 1H-imidazol-1-yl, and n represents 1, and the [(1H-imidazol-1-yl)-methyl] radical corresponding to these meanings is bound to the ring B, one of the symbols X and Y represents epithio and the other the direct bond, the ring A is not substituted, the ring B is not further substituted; and the ring C is unsubstituted or is monosubstituted by chlorine; and the pharmaceutically acceptable monoacid acid addition salts thereof.

7. A compound according to claim 1 corresponding to the formula I given in claim 1, in which Het represents unsubstituted 1H-imidazol-1-yl, and n represents 1, and the [(1H-imidazol-1-yl)-methyl] radical corresponding to these meanings is bound to the ring B, one of the symbols X and Y represents epithio and the other the direct bond, the rings A and C are not substituted and ring B is not further substituted; and the pharmaceutically acceptable monoacid acid addition salts thereof.

8. A compound according to claim 1, which is 1-[(naphtho [1,2-b]thien-4-yl)-methyl]-1H-imidazole and the pharmaceutically acceptable monoacid acid addition salts thereof.

9. A pharmaceutical composition for the treatment of mental depression comprising a therapeutically effective amount of a compound according to claim 1 and having the formula I

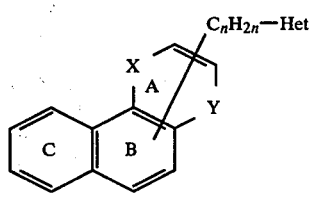

wherein
Het represents 1H-imidazol-1-yl which is unsubstituted or is substituted by lower alkyl,
one of the symbols X and Y represents the epithio radical -S- and the other represents the direct bond, and
n represents 1 to 4, and
besides the substitution of ring A or B by the radical -C$_n$H$_{2n}$-Het, ring A is unsubstituted or is monosubstituted by chlorine or methyl, ring B is unsubstituted or is monosubstituted by chlorine, methyl or methoxy, and ring C is unsubstituted or is monosubstituted by halogen up to atomic number 35, trifluoromethyl, lower alkyl, lower alkoxy or lower alkylthio; or of a pharmaceutically acceptable monoacid acid addition salt thereof, and at least one pharamaceutical excipient.

10. A pharmaceutical composition according to claim 9, wherein a therapeutically effective amount of a compound corresponding to the formula I given in claim 9, in which the radical -C$_n$H$_{2n}$-Het is bound to the ring B and Het, X, Y and n have the meanings defined in claim 9 and the rings A, B and C are unsubstituted or substituted as defined in claim 9, or of a pharmaceutically acceptable monoacid acid addition salt thereof is present.

11. A pharmaceutical composition according to claim 9, wherein a therapeutically effective amount of a compound corresponding to the formula I given in claim 9, in which Het represents 1H-imidazol-1-yl which is unsubstituted or is substituted by methyl, and n is 1 or 2, X and Y have the meanings given in claim 9, the rings A and B, besides being substituted by the radical -C$_n$H$_{2n}$-Het, are not substituted, and ring C is unsubstituted or is monosubstituted by halogen up to atomic number 35, trifluoromethyl, lower alkyl, lower alkoxy or lower alkylthio; or of a pharmaceutical acceptable monoacid acid addition salt thereof is present.

12. A pharmaceutical composition according to claim 9, wherein a therapeutically effective amount of a compound corresponding to the formula I given in claim 9, in which Het represents 1H-imidazol-1-yl which is unsubstituted or is substituted by methyl, and n is 1 or 2, X and Y have the meanings given in claim 9, the ring A is not substituted, the radical -C$_n$H$_{2n}$-Het is bound to the ring B and this ring is not further substituted, and ring C is unsubstituted or is monosubstituted by halogen up to atomic number 35, trifluoromethyl, lower alkyl, lower alkoxy or lower alkylthio; or of a pharmaceutically acceptable monoacid acid addition salt thereof is present.

13. A pharmaceutical composition according to claim 9, wherein a therapeutically effective amount of a compound corresponding to the formula I given in claim 9, in which Het represents unsubstituted 1H-imidazol-1-yl, n represents 1, and one of the symbols X and Y represents epithio and the other the direct bond, the rings A and B, besides being substituted by the radical -C$_n$H$_{2n}$-Het, are not substituted, and the ring C is unsubstituted or is mono-substituted by chlorine; or of a pharmaceutically acceptable monoacid acid addition salt thereof is present.

14. A pharmaceutical composition according to claim 9, wherein a therapeutically effective amount of a compound corresponding to the formula I given in claim 9, in which Het represents unsubstituted 1H-imidazol-1yl, and n represents 1, and the [(1H-imidazol-1-yl)-methyl] radical corresponding to these meanings is bound to the ring B, one of the symbols X and Y represents epithio and the other the direct bond, the rings A and C are not substituted and ring B is not further substituted; or of a pharmaceutically acceptable monoacid acid addition salt thereof is present.

15. A pharamaceutical composition according to claim 9, wherein a therapeutically effective amount of 1-[(naphtho [1,2-b]thien-4-yl)-methyl]-1H-imidazole or of a pharmaceutically acceptable monoacid acid addition salt thereof is present.

16. A method for the treatment of mental depression in a warm-blooded animal comprising enteral or parenteral administration to said animal of a therapeutically effective amount of a compound according to claim 1 having the formula I defined in claim 1, or of a pharmaceutically acceptable monoacid acid addition salt thereof.

* * * * *